United States Patent [19]

Yoshida

[11] Patent Number: Plant 5,884

[45] Date of Patent: Feb. 17, 1987

[54] AFRICAN VIOLET (VARIETY—EILEEN)

[76] Inventor: Eiichi Yoshida, P.O. Box 4836, Hayward, Calif. 94540-4836

[21] Appl. No.: 726,830

[22] Filed: Apr. 24, 1985

[51] Int. Cl.[4] ..... A01H 5/00

[52] U.S. Cl. ..... Plt./69

[58] Field of Search ..... Plt./69

*Primary Examiner*—Robert E. Bagwill

[57] ABSTRACT

A new variety of African violet plant for potted plant culture particularly distinguished by its year around blooming capability, its profuse production of clear white with distinct violet blue edged flowers, and its abundant foliage of solid green color which provide a spreading base and attractive backing for the clusters of blossoms.

1 Drawing Figure

BACKGROUND OF THE NEW PLANT

This new variety of African violet plant was discovered by me in 1983 after crossing Seed Parent Melodie Mitzi and Pollen Parent Kleiber Hybrid BWG3, at Hayward, Calif. With subsequent propagation of the new plant by means of leaf cuttings at Hayward, Calif., this plant has demonstrated that its distinctive characteristics hold true from generation to generation and appear to be firmly fixed.

DESCRIPTION OF THE PLANT

Sheet one is a full color photographic view of the plant in bloom. The colors shown being as nearly true as it is reasonably possible to obtain by conventional photographic procedures.

The following is a detailed description of my new African violet plant with the color designation being according to The R.H.S. Colour Chart published by The Royal Horticultural Society of London, England, with collaboration by The British Colour Council.

THE PLANT

Origin: Seedling, #H-551/3.

Seed parent: Melodie Mitzi.

Pollen parent: Kleiber hybrid BWG3.

Classification:

*Botanic.*—*Saintpaulia inonanthe.*

*Commercial.*—African violet.

Form: Rosette arrangement.

Height: 10.3 to 12.6 cm. tall.

Growth: New growth is vigorous and has a tendency to grow slightly upwards. As leaves get older, they grow more horizontally and eventually grow somewhat downward.

Size: Large, overall plant diameter is from 24 to 25.3 cm.

Mutation prone: Very little for foliage. An occasional solid flowering plant is produced.

Foliage: Abundant in quantity, brittle.

*Shape.*—Oval with slight crenate margins.

*Length.*—Approximately 7 cm. for a mature leaf.

*Width.*—Approximately 7.3 cm. for a mature leaf.

*Color.*—Upper side: Medium Green. Underside: Light Green.

*Texture.*—Upperside: Pubescent. Underside: Puberulent.

*Ribs and veins.*—Veins are pinnate, slightly sunken on leaf surface, pronounced on underside of leaf.

*Petiole.*—Round, light green, pubescent on its upper and puberulent on its underside. Length varies with age of leaf and plant.

Flower:

*Blooming habit.*—Continuous and abundant under optimum growing conditions.

*Number.*—Eight to ten per peduncle.

*Size.*—Each flower is approximately 4.2 cm. in diameter.

*Color.*—Flower center is White Group, 155-A; flower edge is Violet Group, 88-A, from The R.H.S. Colour Chart.

*Type.*—Single.

*Petals.*—Five per individual flower with ruffled margins.

*Texture.*—Smooth and flexible.

*Appearance.*—Glittery upper and underside. Underside is sparsely puberulent.

*Peduncles.*—Short, strong, puberulent.

*Inflorescence.*—Cyme, upright, above foliage.

*Calyx.*—Quinquepartite, puberulent.

*Persistence.*—Flowers do not drop. Old flowers dry up on the stalk.

*Fragrance.*—None.

Reproductive organs:

*Stamens.*—Usually two per flower and joined at top of anthers.

*Anthers.*—Visible, bright yellow, fade slightly as they get older; one on each filament.

*Filaments.*—Approximately 0.3 cm. long.

*Pollen.*—Light yellow, ripens before stigma.

*Pistils.*—Normally seven per flower.

*Stigma.*—Usually visible and accessible. When receptive, it becomes swollen and usually exudes a small drop of clear fluid.

*Style.*—Approximately 0.7 cm. long.

*Ovary.*—Superior.

This variety of African violet plant is very suited for potted plant culture and its year around blooming capability gives the plant a commercially attractive value. Flowers do not drop in cool temperature. This new African violet is a good producer that is fairly disease resistant. One of the most important characteristic of this variety of African violet is that of uniformity. Uniformity and reliability are found at every point in the growing of this variety. In plants initiated at one time from leaf cuttings virtually all plantlets uniformly come up at the same time and bloom at the same time following the planting.

I claim:

1. An African violet plant having violet blue-edged white flowers and abundant foliage.

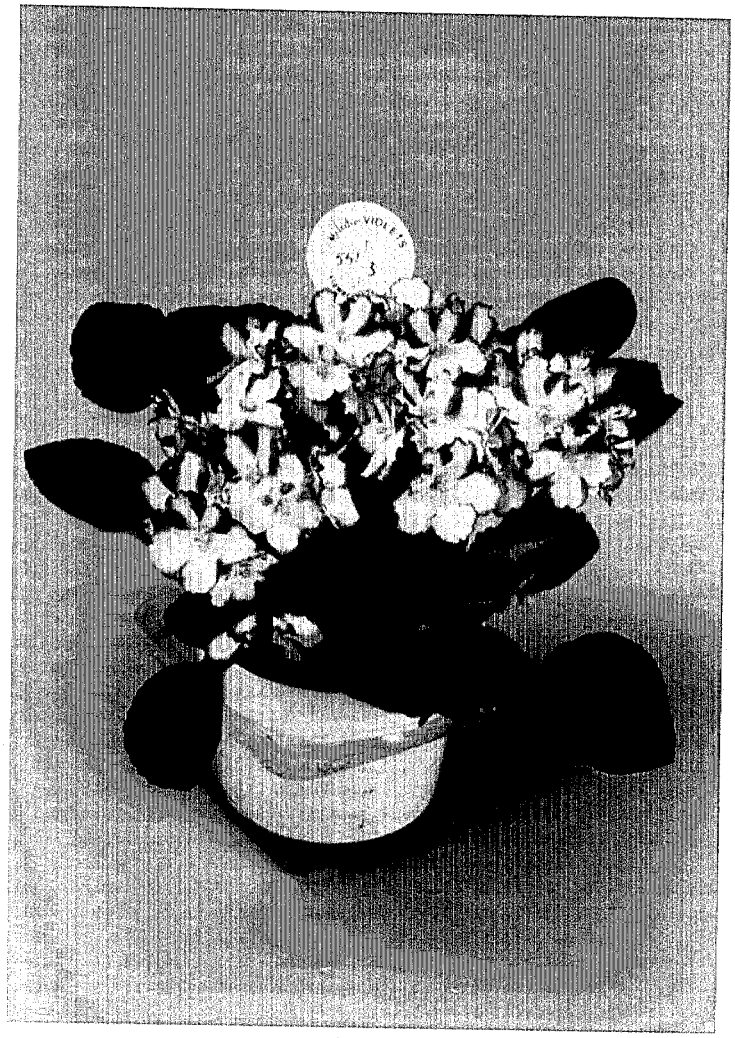

* * * * *